(12) United States Patent
Zohar

(10) Patent No.: US 9,649,067 B2
(45) Date of Patent: May 16, 2017

(54) PULSE-MONITORED, VIBRATING VEHICLE SEAT MECHANISM

(71) Applicant: Tedi Zohar, Long Beach, CA (US)

(72) Inventor: Tedi Zohar, Long Beach, CA (US)

( * ) Notice: Subject to any disclaimer, the term of this patent is extended or adjusted under 35 U.S.C. 154(b) by 0 days.

(21) Appl. No.: 14/998,018

(22) Filed: Aug. 12, 2014

(65) Prior Publication Data
US 2016/0354026 A1 Dec. 8, 2016

Related U.S. Application Data

(60) Provisional application No. 61/967,327, filed on Mar. 14, 2014.

(51) Int. Cl.
| G08B 23/00 | (2006.01) |
| A61B 5/00 | (2006.01) |
| B60N 2/44 | (2006.01) |
| B60W 50/16 | (2012.01) |
| A61B 5/11 | (2006.01) |
| B60W 50/14 | (2012.01) |
| G08B 6/00 | (2006.01) |
| A61M 21/00 | (2006.01) |

(52) U.S. Cl.
CPC ........... *A61B 5/6893* (2013.01); *A61M 21/00* (2013.01); *A61M 21/0094* (2013.01); *B60N 2/448* (2013.01); *B60W 50/16* (2013.01); *A61B 5/0022* (2013.01); *A61B 5/1112* (2013.01); *A61M 2021/0022* (2013.01); *A61M 2021/0055* (2013.01); *A61M 2021/0083* (2013.01); *A61M 2205/18* (2013.01); *A61M 2205/50* (2013.01); *A61M 2230/06* (2013.01); *B60N 2002/4485* (2013.01); *B60W 2050/143* (2013.01); *B60W 2050/146* (2013.01); *B60W 2540/26* (2013.01); *G08B 6/00* (2013.01)

(58) Field of Classification Search
CPC .................................. G08B 1/00; A61B 1/00
See application file for complete search history.

(56) References Cited

U.S. PATENT DOCUMENTS

2014/0275834 A1* 9/2014 Bennett .................. B60N 2/502
600/301

* cited by examiner

*Primary Examiner* — Shirley Lu

(57) ABSTRACT

A Pulse-Monitored, Vibrating Vehicle Seat Mechanism is a drowsiness alert system. The Pulse-Monitored, Vibrating Vehicle Seat Mechanism consists of cardiac sensors, a vibration device encased in the vehicle seat upholstery, and communication elements. The mechanism is powered by the electrical system of the given vehicle and can be integrated inside any vehicle.

13 Claims, 7 Drawing Sheets

PULSE-MONITORED, VIBRATING VEHICLE SEAT MECHANISM

CROSS-REFERENCE TO RELATED APPLICATIONS

61/967,327; 61/966,713; 61/795,745; 61/848,394; 61/855,222; 13/918,945

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The present invention is in the technical field of vehicle seat mechanisms. More particularly, the present invention is in the technical field of pulse-monitored, vibrating vehicle seat mechanisms. Specifically, this invention relates to a drowsiness warning system which monitors the user's heart rate and activates vibration when the user's heart rate falls below a calculated, predetermined percentage below the user's resting heart rate.

BACKGROUND OF THE INVENTION

Conventional alarms such as alarm clocks, cell phones, digital watches are only useful when set to a certain time specification. However, what if sleep overcomes a person who has neglected to set the traditional wake up device? Furthermore, what if sleep overwhelms one who is acting in a situation where sleep is inappropriate? There are many different scenarios in society where drowsiness and sleep are a hazard. For example, a cross-country, long haul truck driver would jeopardize his own life as well as the life of others if he succumbs to sleep. For the driver to anticipate the exact moment when sleep will occur is impossible. Therefore, to predict sleep and be prepared by setting an alarm is not feasible. For the safety of the driver and others on the road, the truck driver must be awake and alert. Another example is a pilot on an international flight. Long hours and multiple connecting flights during international travel can increase drowsiness and fatigue for the pilot. Many lives depend on his/her awareness to communicate and his/her ability to stay focused and alert. Drowsiness and sleep during his/her watch could lead to an accident or loss of life. In addition, a night shift worker on his/her way home in the early hours of morning after a 12 hour shift may be challenged with staying awake on the drive home. Driving home may be a monotonous task after the stress of a night's work, and the shift worker can become drowsy. If the worker falls asleep, this can lead to unsafe driving and the commute home could become deadly.

Drowsiness and lack of awareness can have a critical impact in the case of many professions: military, nursing, transportation, education, security and criminal justice, as well as, the general population who may engage in an activity that will put the person or others in harm's way if sleep occurs while driving or operating a vehicle of another nature such as a train, a plane, or a watercraft. When a mechanism can detect physical manifestations of sleep and respond to that change, unwanted sleep can be avoided.

SUMMARY OF THE INVENTION

The present invention is a vehicle mechanism that monitors the heart rate of its operator; when the pulse decreases below the resting heart rate which is an indicator of sleep, the seat vibrates to restore the user to the state of being alert. The human heart rate can be affected by many variables. Each individual has a resting heart rate that is unique to that individual. An individual's resting heart rate can change over a lifetime based on how physically active the person is, the amount of stress one is facing, and numerous other weighted factors. The average range of a resting heart rate ranges from 50 to 85 beats per minute. Another factor that alters heart rate is the onset of sleepiness.

For a majority of the population, the onset of sleep drops the pulse rate between 55 to 65 beats per minute. The average reduction of pulse rate during sleep is 8%. However, if that percentage of decrease has been reached, the awareness and alertness of the individual has been compromised. Therefore, the warning to the individual must occur before the full onset of sleep. To review the function of this mechanism, once the mechanism is activated, it will calibrate to the average resting heart rate of the individual. If the heart rate decreases the specified percentage below the user's average resting heart rate; then, the alarm triggers and vibration waves stimulate the user through all points of contact with the seat. This alerts the user of the onset of sleep and the individual may then take the appropriate precautions for safety in his or her given situation.

Furthermore, the strength of the vibration necessary for effectiveness will vary from individual to individual. Therefore, the vibration mode will be adjustable to be customized to the need of each user. There will be 10 levels of vibration that will activate at a specified level then escalate to the desired full effect for the individual as to not startle the individual. The device will activate 3 levels below the desired "awake" level. For example, a young female may select the desired vibration level 6. As the device is activated by the reduction of pulse rate, the device will activate at level 3 and build steadily to level 6 to restore the individual to full awareness. For another example of custom vibration, a middle-aged male may preset the vibration level to 10. For him, the device would activate at level 7 and build to level 10 for maximum individual effectiveness.

When an individual first activates the vehicle, the mechanism will calibrate to the user's heart rate. The wireless cardiac sensors will detect the user's average heart rate and monitor the heart rate throughout the usage of the device. The heart rate data is collected through the use of wireless sensors in the vehicle and shared through communication with a parent device. As soon as the device calibrates, it will signal to the user to set the vibration level. The device will fire at level 1; then the user can increase the level for individual optimum effectiveness. If the user does not set the vibration level, the device will default to a median preset level 6

If the wireless cardiac does not receive input for pulse detection within 90 seconds, the mechanism hibernates. Also, the mechanism is disabled when the ignition of the vehicle is switched to the "off" position. The mechanism will retain the settings for this individual until another user calibrates the device for his/her use.

Furthermore, a flash memory records the time and date of each "fired" vibration warning of the mechanism as a record of the user's sleepiness patterns. The data can be retained in the flash memory and transferred and recorded in cloud storage. When the mechanism is calibrated for a new user, the calibration is reset and the device will begin logging data for the new user.

Due to the device's Bluetooth and Wi-Fi capabilities, the mechanism can communicate, share information with and be controlled by other electronic devices such as, but not limited to: SMART phones, SMART watches, SMART bracelets, tablets, laptops, Mobile/Software Application (APP), GPS, or Bluetooth capable audio/stereo systems and or/ computerized car systems.

The mechanism is powered by the electrical system of the given vehicle, and this mechanism can be integrated inside any vehicle.

The invention functions as a universal, pulse-monitored, vibrating vehicle seat mechanism. It includes switches for on/off and plus/minus which controls this device. There are a few ways to control the device, for example: 1) through the user preferred parent control device: the user opens a Mobile/Software Application (APP) and begins to control the device. 2) the user utilizes an integrated software within the parent device, or 3) the user can operate the mechanism independently through an integrated software within a control panel. Next, mechanism calibrates and it establishes the user's average pulse rate. Then, the user sets the customized vibration level for his/her usage. The micro-USB port is also located on the control panel.

DETAILED DESCRIPTION OF THE INVENTION

Figure 1:
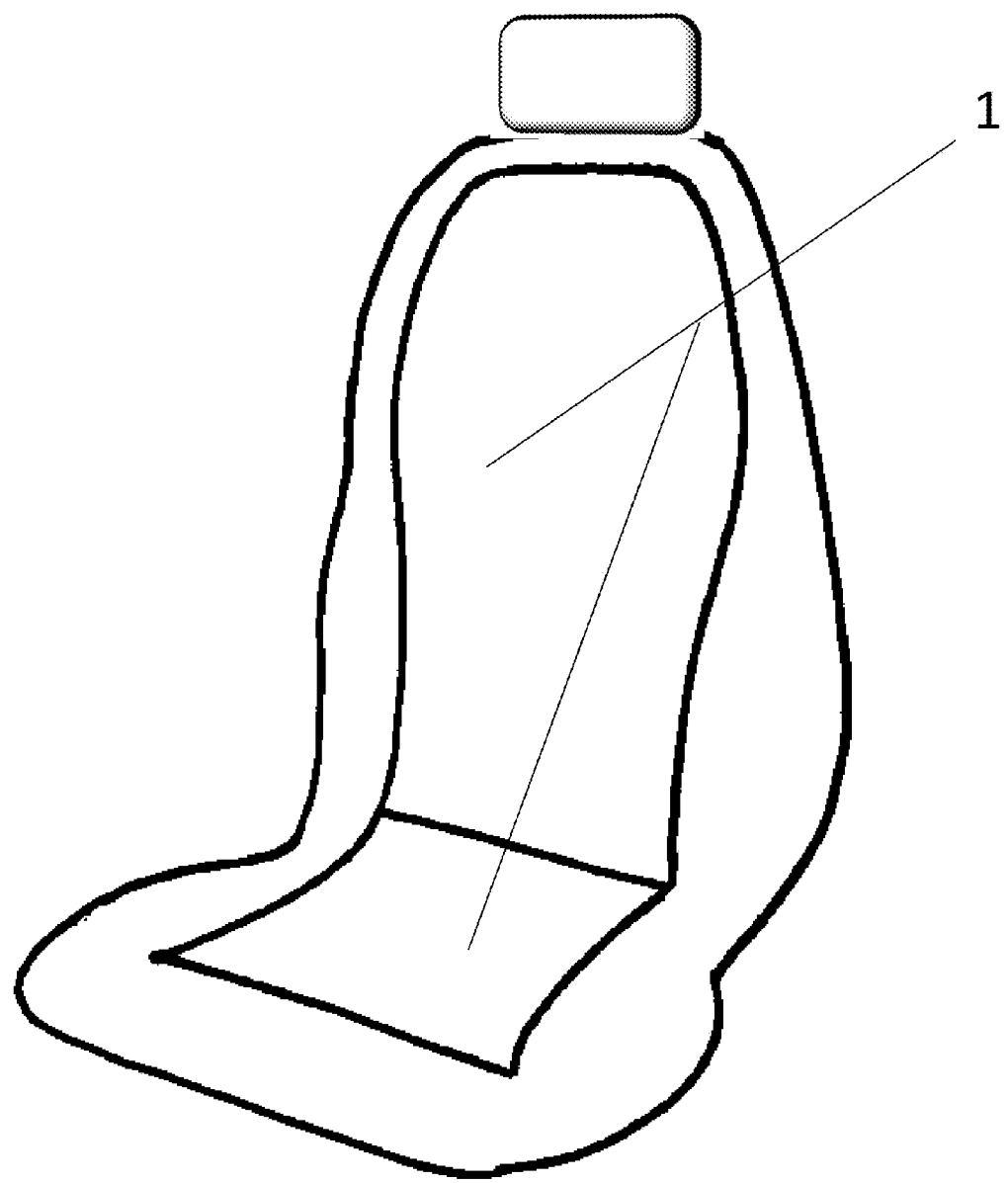
FIG. 1 is a perspective view of the anterior of the Pulse-Monitored, Vibrating Vehicle Seat Mechanism.
Figure 2:
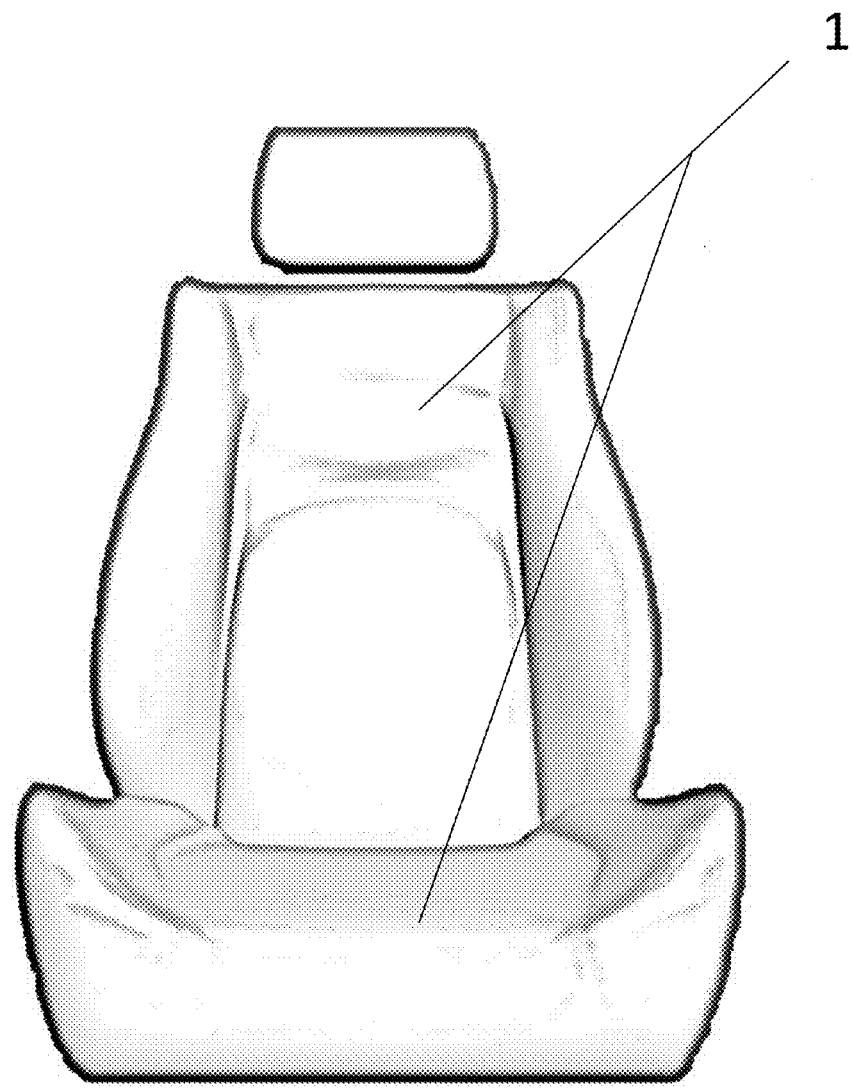
FIG. 2 is a front elevation view of the Pulse-Monitored, Vibrating Vehicle Seat Mechanism of FIG. 1.

FIG. 1 shows the perspective view of the anterior of the Pulse-Monitored, Vibrating Vehicle Seat Mechanism. FIG. 2 is a front elevation view of the Pulse-Monitored, Vibrating Vehicle Seat Mechanism of FIG. 1. The Pulse-Monitored, Vibrating Vehicle Seat Mechanism is composed of a massage device, wireless cardiac sensors, and padding encased in the seat cover upholstery. The mechanism is powered by the electrical system of the given vehicle, and this mechanism can be integrated in any vehicle.

In further detail of the invention shown in FIG. 1 and FIG. 2, the pulse-monitored, Vibrating Vehicle Seat Mechanism 1 is of sufficient size to be universal to all vehicle seats that have a seating platform and a back rest.

The construction details of the invention as shown in FIG. 1 and FIG. 2 are that the present mechanism may be made of sufficiently durable materials such as fabric, foam, high strength plastic, metal, vehicle upholstery and the like.

Figure 3:
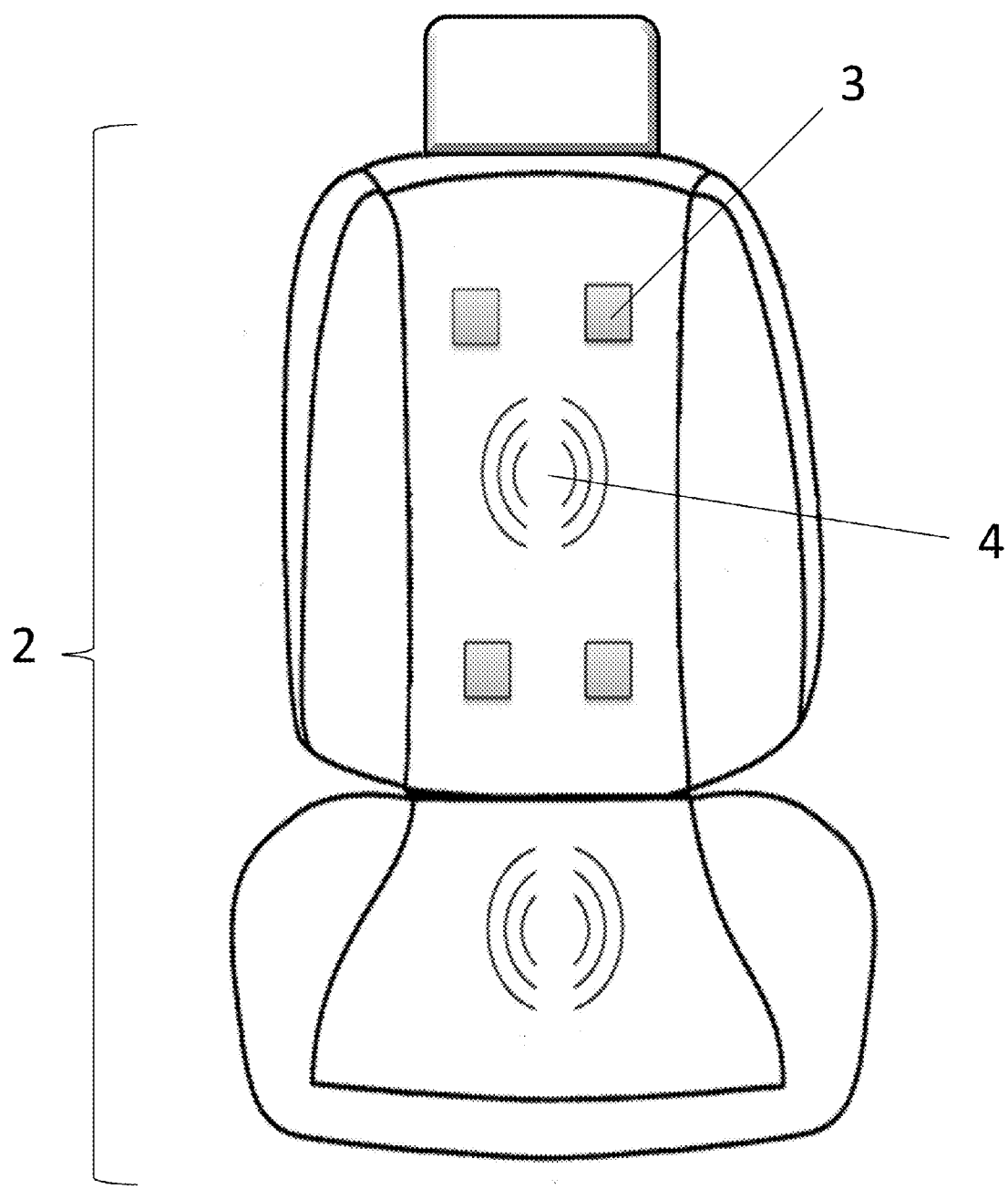
FIG. 3 is a front sectional view embodiment of the active exterior of the Pulse-Monitored, Vibrating Vehicle Seat Mechanism of FIG. 1.
Figure 4:
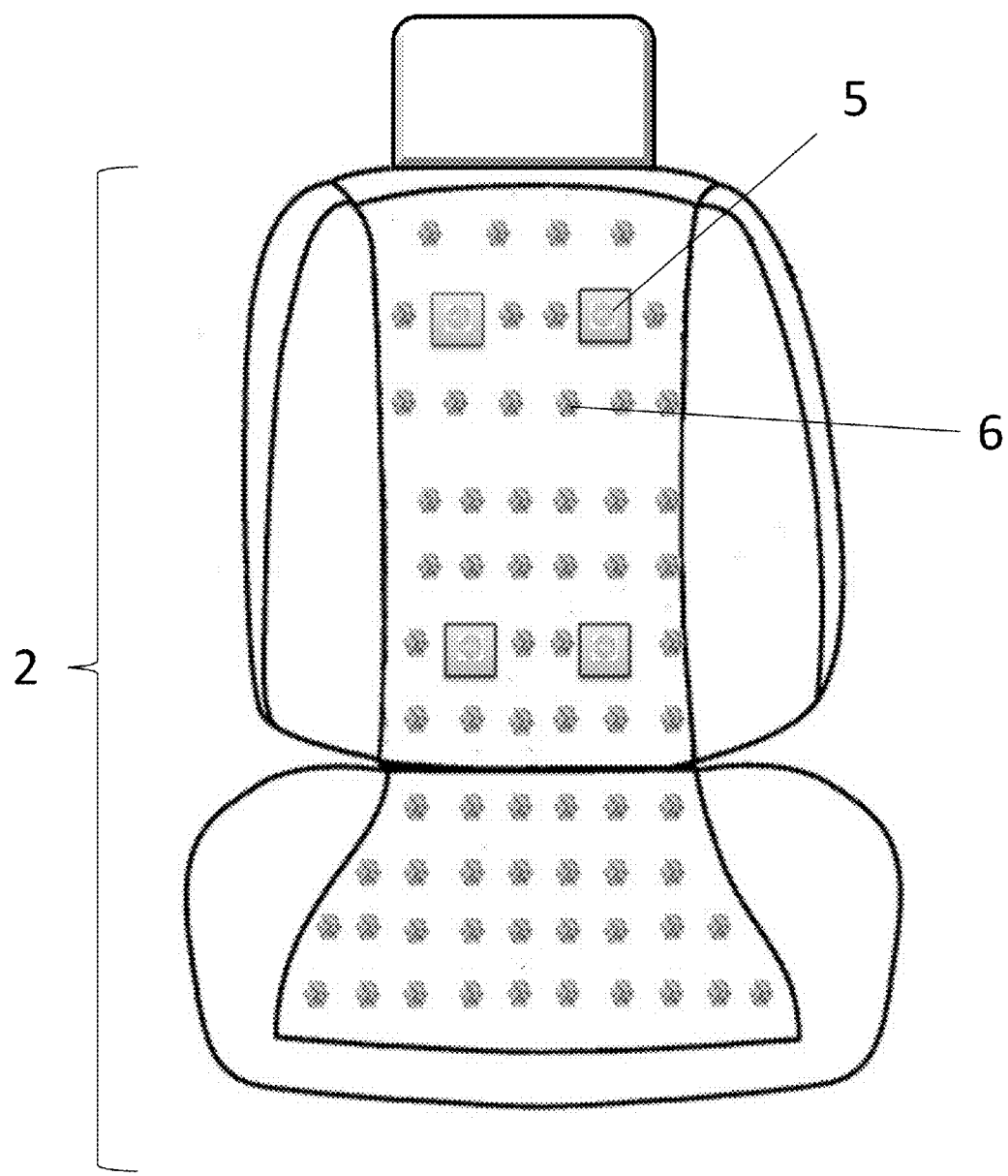
FIG. 4 is the front sectional view of the internal mechanism of the Pulse-Monitored, Vibrating Vehicle Seat Mechanism of FIG. 1.

Referring now to FIG. 3 and FIG. 4, there is shown the embodiment of the active exterior of the pulse-monitored, vibrating seat mechanism 2 and internal components of this device. FIG. 3 represents the external location of the wireless cardiac sensors 3 and demonstrates the vibrational capacity of the device 4. FIG. 4 details the inner placement of the cardiac sensors 5 and the surface level view of the vibrational mechanism 6 of the device in the present invention.

In more detail, still referring to the invention in FIG. 4, the wireless cardiac sensors 5 are round and approximately the size of a quarter: Diameter—24.26 mm. The vibrational mechanism 6 consists of internal vibrating pads that are distributed evenly over the surface of the seating area of the present mechanism.

The construction details of the invention as shown in FIG. 3 and FIG. 4 are that the present mechanism may be made out of sufficiently rigid and strong materials such as high-strength plastic, metal, silicone, foam, neoprene, vehicle upholstery and the like. Furthermore, the various components of the inner mechanism can be made of different materials.

Figure 5:
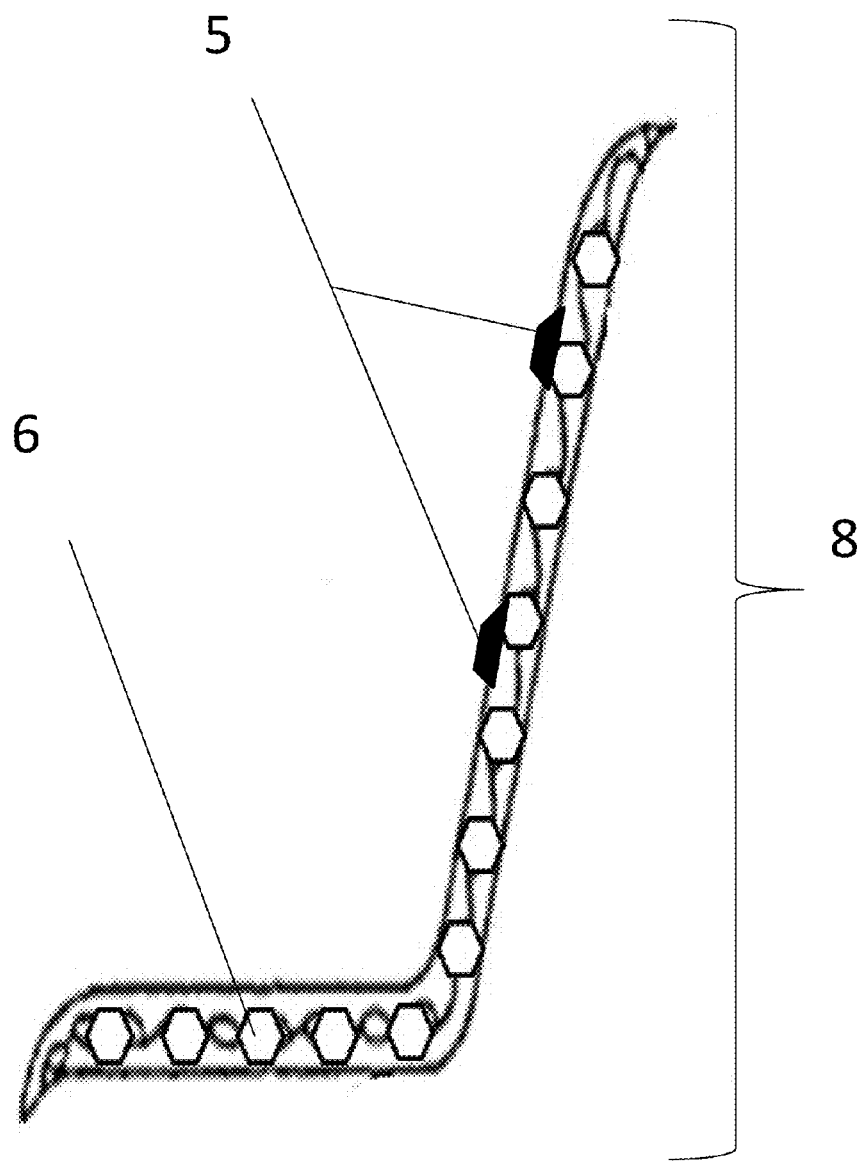
FIG. 5 is the side sectional view of the Pulse-Monitored, Vibrating Vehicle Seat Mechanism of FIG. 1.

Referring now to FIG. 5, there is shown side sectional view 8 of the Pulse-Monitored, Vibrating Vehicle Seat Mechanism. FIG. 5 shows the internal, sectional view of the device. FIG. 5 illustrates the vibrating mechanism 6 distributed throughout the device. FIG. 5 also depicts the sectional view of the placement of the wireless cardiac sensors 5 within this present mechanism.

In more detail, still referring to the invention in FIG. 5, the wireless cardiac sensors 5 are round with an approximate thickness of 2-3 mm. The vibrational element 6 of the internal vibration device will be placed evenly underneath the surface of the seating area of the present mechanism.

The construction details of the invention as shown in FIG. 5 are that the present mechanism may be made out of sufficiently rigid and strong materials such as high-strength plastic, metal, silicone, foam, neoprene, and the like. Furthermore, the various components of the inner mechanism can be made of different materials as appropriate to the technology, therein.

Figure 6:
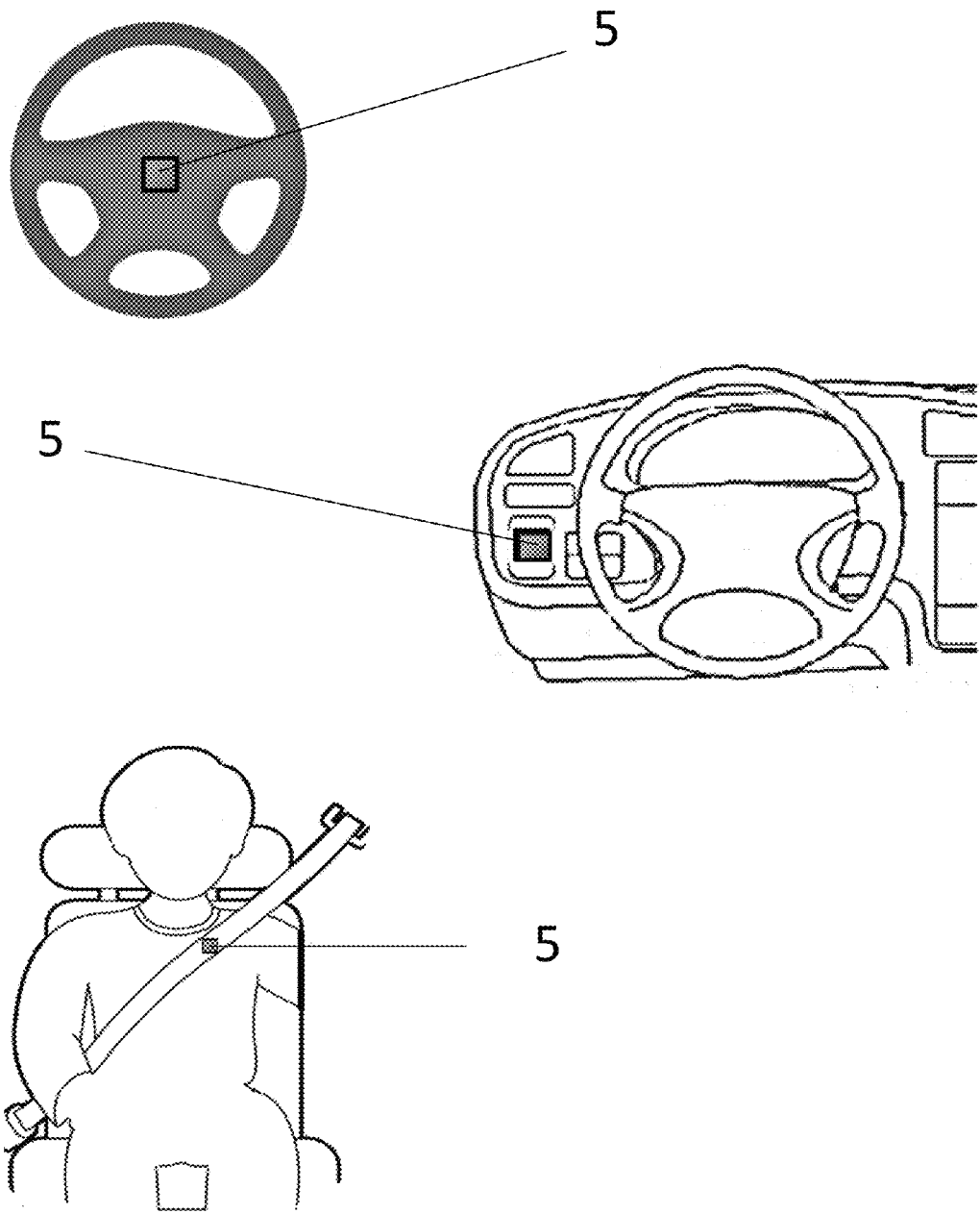
FIG. 6 is the front elevation view of possible variations of the positioning of the wireless cardiac sensors within the Pulse-Monitored, Vibrating Vehicle Seat Mechanism.

Referring now to FIG. 6, there is shown variants for placement of the wireless cardiac sensors 5 within a vehicle. The wireless cardiac sensors may be placed anywhere inside the vehicle within optimum, accurate reporting distance from the operator In more detail, still referring to the invention as shown in FIG. 6, the wireless cardiac sensors may be positioned in the vehicle steering wheel, on the dashboard, within the operator's vehicle safety restraint as shown in FIG. 6, or anywhere inside the vehicle within optimum, accurate reporting distance from the operator In more detail, still referring to the invention in FIG. 6, the wireless cardiac sensors 5 are round with an approximate thickness of 2-3 mm.

Figure 7:
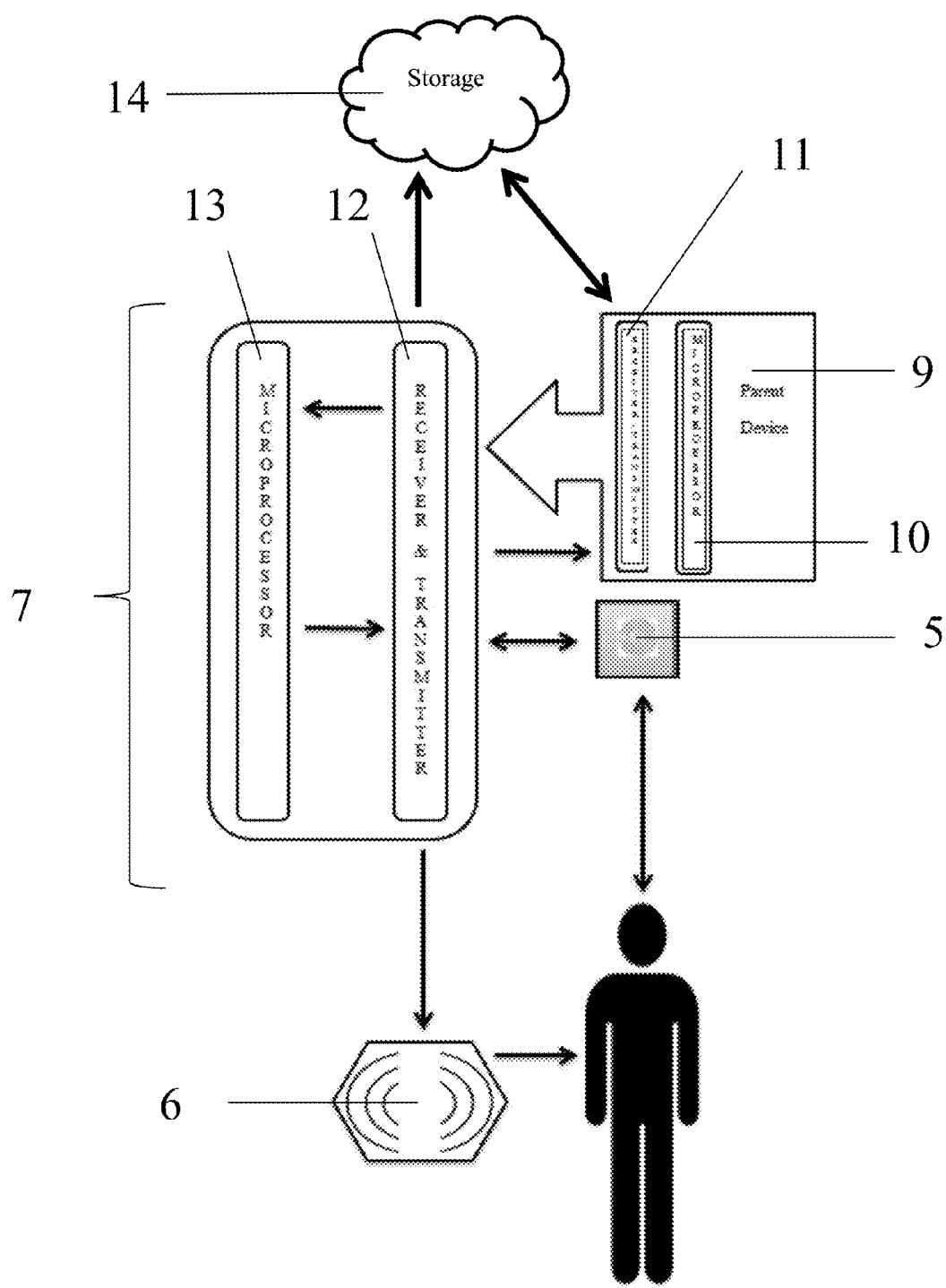
FIG. 7 is a flow chart view of the Pulse-Monitored, Vibrating Vehicle Seat Mechanism of FIG. 1 in accordance with one aspect of the invention.

Referring now to FIG. 7, there is shown a flow chart view of the Pulse-Monitored, Vibrating Vehicle Seat Mechanism of FIG. 1 in accordance with one aspect of the invention. FIG. 7 details the flow chart view of the control panel 7 of this present device: the receiver and transmitter 12, the microprocessor 13, the wireless cardiac sensors 5, the vibrating mechanism 6, and the remote cloud storage 14 of the Pulse-Monitored, Vibrating Vehicle Seat Mechanism. FIG. 7 also illustrates a communicating parent device 9 with a microprocessor 10 and a receiver and transmitter 11.

In more detail, still referring to the invention in FIG. 7 in accordance with one aspect of the invention, the parent device 9 of this mechanism can control this mechanism remotely and can be defined as: devices such as, but not limited to: SMART phones, SMART watches, SMART bracelet, tablet, laptop, a SMART Application, GPS, automobile audio/stereo systems, computerized car systems, and other accessories designed to work with this portable drowsiness warning system through Wi-Fi and Bluetooth technologies. When the user begins the calibration of the present mechanism, the parent device 9 sends the signal via the transmitter/receiver 11 to the transmitter/receiver 12 of the present device. The receiver/transmitter 12 passes the signal to the microprocessor 13. The microprocessor 13 sends the signal to the wireless cardiac sensors 5 to activate the heart rate monitoring which continues throughout the usage of the device. The wireless cardiac sensors send continuous information to the microprocessor 13. The microprocessor 13 sends the data that is collected through the receiver/transmitter 12 to the receiver/transmitter 11 which relays the data to the microprocessor 10 of the parent device 9. The microprocessor 10 then sends the information of the heart rate monitoring to be viewed on the display parent device 9. The process of collecting and displaying data is ongoing throughout the use of this present mechanism.

Still, in more detail, referring to the invention in FIG. 7 in accordance with one aspect of the invention, once the heart rate monitoring has been established by this present mechanism, the parent device 9 sends another signal via the transmitter/receiver 11 to the transmitter/receiver 12 of the present mechanism. The receiver/transmitter 12 passes the signal to the microprocessor 13. The microprocessor 13 sends the signal to the vibrating mechanism 6 to activate vibration. The parent device 9 displays information to the user to set the comfortable level of vibration. When the vibrations initiates, the user uses the parent device to increase the level of vibration to the highest level between 1 and 10 that will be the optimum vibration level for the individual. Once calibration is complete, the Pulse-Monitored, Vibrating Vehicle Seat Mechanism continues with the ongoing cycle of collecting and the displaying data throughout the use of this present mechanism.

Referring still to the invention in FIG. 7 in accordance with one aspect of the invention, during the use of this present mechanism when the user's heart rate drops a specified percentage below the resting heart rate, the microprocessor 13 signals to the vibrating mechanism 6 to activate. The vibration mechanism 6 continues to be active until it receives the signal to end vibration. When the pulse rate returns to the average heart rate range, the microprocessor 13 sends a command to the vibrating mechanism 6 to cease vibration. At the same time, the data collected during the period of reduced heart rate will be sent by the microprocessor 13 through the transmitter 12 to be saved in the remote cloud storage 14 which can later be accessed by the parent device 9. The present device will continue the active monitoring of the heart rate until the user terminates the function through the parent device or until the pulse rate data cannot be collected for a period of time longer than 90 seconds; for example, the user is no longer in range of the wireless cardiac sensors 5 because he/she has left the vehicle.

The construction details of the invention as shown in FIG. 7 are that the present mechanism may be made out of sufficiently rigid and strong materials such as high-strength plastic, metal, silicone, foam, neoprene, vehicle upholstery and the like. Furthermore, the various components of the inner mechanism can be made of different materials as appropriate to the technology, therein.

The advantages of the present invention include, without limitation that the mechanism is dependable. The vibration elements are comfortable and able to be customized and integrated into any seat. The mechanism is easy to set and can function independently or be controlled by an external parent device through integrated software and/or a mobile/software application (APP). Moreover, the present mechanism is weather, sweat, and water resistant. The mechanism has application for all sectors of society—civilian to military, or for any situation when it is vital for one to stay awake and alert.

In broad embodiment, the present invention is an integrated drowsiness warning seat mechanism which monitors the user's pulse rate and activates the vibration mode when the user's pulse rate falls below a calculated, predetermined percentage below the user's resting heart rate; the Pulse-Monitored, Vibrating Vehicle Seat Mechanism functions independently or in communication with personal devices such as, but not limited to: SMART phones, SMART watches, SMART bracelet, tablet, laptop, a Mobile/Software Application (APP), GPS, automobile audio/stereo systems, computerized car systems, and other accessories designed to work with this drowsiness warning system through Wi-Fi and Bluetooth technologies.

While the foregoing written description of the invention enables one of ordinary skills to make use of what is considered presently to be best mode thereof, those of ordinary skill will understand and appreciate the existence of variations, combinations, and equivocations of the specific embodiment, method, and examples herein. The invention should therefore not be limited by the above described embodiment, method, and examples, but by all embodiments and methods within the scope and spirit of the invention as claimed.

What is claimed is:

1. A pulse-monitored, vibrating vehicle seat system, comprising:
A mechanism monitoring the heart-rate of a user, vibrating pads, wireless heart rate sensors, bioelectrical cable, microprocessor, flash memory, control panel, micro-USB port, Wi-Fi and Bluetooth;
wherein when the heart rate of a user slows to a calculated rate below the user's average, resting heart rate, which is an indicator of drowsiness or the onset of sleep, the mechanism activates silent, electric pulse stimuli at an accelerating rate from levels low to high; wherein the electric pulse stimuli is set by the user; wherein the user sets customized, predetermined levels when the user calibrates the device at the initiation of operating the vehicle; wherein when the user activates the system;
wherein a control panel activates and signals to the microprocessor to engage heart rate sensors;
wherein the heart rate sensors gather pulse rate data and transmit the pulse rate data to the microprocessor;
wherein the heart rate sensors are placed anywhere inside the vehicle within optimum, accurate reporting distance from the user;
wherein the microprocessor begins calibration to establish the baseline resting heart rate for the user;
wherein the control panel displays heart rate data and then prompts the user to adjust and set the level of vibration of maximum comfort for the desired highest level of vibration for the user;

wherein the microprocessor records data as monitoring of heart rate data continues;

wherein when the resting heart rate falls to a rate calculated by a predetermined formula of a percentage drop of beats below the user's resting heart rate, the microprocessor sends a command to the vibration pad mechanism to generate a silent vibrating alarm;

wherein when the resting heart rate falls to a rate calculated by a predetermined formula of a percentage drop of beats below the user's resting heart rate a silent vibrating alarm is generated, the seat mechanism vibrates, and the vibrating pads initiates three vibration levels below the user's level of vibration of maximum comfort, then increases to the user's level of vibration of maximum comfort for the desired highest level of vibration for the user;

wherein as the seat mechanism vibrates, the microprocessor continues to collect data from the heart rate sensors as continuous heart rate monitoring continues;

wherein the microprocessor sends a command to the vibration pad mechanism to cease vibration when The pulse increases to a preset threshold above the resting heart rate;

wherein the control panel allows the level of vibration and heart rate levels to be saved at any time during usage;

wherein the control panel records modifications to the flash memory, and transmits and stores device data to cloud storage through Wi-Fi or Bluetooth technologies;

wherein flash memory records data of when the mechanism alarms, and maintains records of all user modifications, date, and time to the flash memory;

wherein the mechanism data is transmitted and archived in cloud storage through Web Portal, or Mobile/Software Application (APP) through Wi-Fi or Bluetooth technologies;

wherein the cloud storage is accessed through electronic devices, such as SMART phones, SMART watches, SMART bracelet, tablet, laptop, a Mobile/Software Application (APP), GPS, computerized car systems and other electronic devices and accessories designed to work with the system;

wherein the system functions within two separate operational MODES: WORK and SLEEP;

wherein when the vehicle engine becomes active, the pulse-monitored, vibrating vehicle seat system functions in WORK MODE as the default setting for vehicle usage and may not be disabled by the user when the vehicle ignition has been activated;

wherein when the system is set to SLEEP MODE, the present invention disables the pulse monitoring feature and functions as a digital clock that can be set for a specific time as a silent or audible, vibrating alarm clock within the vehicle;

wherein the SLEEP MODE can only be manually engaged when the vehicle key is in the vehicle ignition, or the electrical components of the vehicle are engaged, but the vehicle engine is not activated.

2. The pulse-monitored, vibrating vehicle seat system of claim 1, wherein the micro-USB port is used to download information from the mechanism or to upload data to the mechanism.

3. The pulse-monitored, vibrating vehicle seat system of claim 1, wherein the Wi-Fi capabilities of the mechanism shares data and interaction with other Wi-Fi enabled devices.

4. The pulse-monitored, vibrating vehicle seat system of claim 1, wherein the Bluetooth capabilities of the mechanism shares data and interaction with other Bluetooth enabled devices.

5. The pulse-monitored, vibrating vehicle seat system of claim 1, wherein the mechanism communicates with other devices through Wi-Fi and Bluetooth technologies.

6. The pulse-monitored, vibrating vehicle seat system of claim 1, wherein the mechanism receives communications from satellites via GPS;

wherein GPS provides vehicle location data;

wherein the vehicle location data is transferred through Wi-Fi and/or Bluetooth and recorded to a cloud storage, web portal, or Mobile/Software Application (APP).

7. The pulse-monitored, vibrating vehicle seat system of claim 1, wherein the mechanism receives communication from satellites, Wi-Fi and Bluetooth technologies by federal digital emergency alert systems.

8. The pulse-monitored, vibrating vehicle seat system of claim 1, wherein the data archived from the device is accessed by the user or a third party through the cloud storage, web portal, or Mobile/Software Application (APP).

9. The pulse-monitored, vibrating vehicle seat system of claim 8, wherein includes a feature for sound/music in addition to vibration can he selected in both MODES through the control panel; wherein the modes are labeled WORK MODE: Audio "On/Off" and SLEEP MODE: Audio "On/Off".

10. The pulse-monitored., vibrating vehicle seat system of claim 1, wherein the power source is integrated into the electrical system of the vehicle, and the mechanism can be integrated into any vehicle.

11. The pulse-monitored, vibrating vehicle seat system of claim 1, wherein the vibrating mechanism and vibrating pads have 10 distinct vibration levels; wherein the levels are identified as and labeled 1-10; wherein once the vibration activates at level 1, the user can increase and select his/her preferred level for individual optimum effectiveness; wherein if the user does not set the vibration level, the device will default to a preset level.

12. The pulse-monitored, vibrating vehicle seat system of claim 1, wherein the wireless cardiac sensors can be placed anywhere inside the vehicle within optimum, accurate reporting distance from the user.

13. The pulse-monitored, vibrating vehicle seat system of claim 1, wherein the vibrating. mechanism and vibrating pads can operate independently in preset or random pulsing, patterns, separately or together in unison.

* * * * *